US012636060B2

(12) United States Patent
Allen, IV et al.

(10) Patent No.: US 12,636,060 B2
(45) Date of Patent: May 26, 2026

(54) ELECTROSURGICAL INSTRUMENTS, SYSTEMS, AND METHODS INCLUDING USE OF THERMAL CUTTING ELEMENTS

(71) Applicant: Covidien LP, Mansfield, MA (US)

(72) Inventors: James D. Allen, IV, Broomfield, CO (US); William E. Robinson, Boulder, CO (US); Daniel A. Joseph, Golden, CO (US); John A Hammerland, III, Arvada, CO (US); Kenneth E. Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 357 days.

(21) Appl. No.: 18/019,932

(22) PCT Filed: Aug. 11, 2021

(86) PCT No.: PCT/US2021/045549
§ 371 (c)(1),
(2) Date: Feb. 6, 2023

(87) PCT Pub. No.: WO2022/046414
PCT Pub. Date: Mar. 3, 2022

(65) Prior Publication Data
US 2023/0285064 A1 Sep. 14, 2023

Related U.S. Application Data

(60) Provisional application No. 63/072,784, filed on Aug. 31, 2020.

(51) Int. Cl.
*A61B 18/08* (2006.01)
*A61B 18/14* (2006.01)
(Continued)

(52) U.S. Cl.
CPC ........ *A61B 18/085* (2013.01); *A61B 18/1445* (2013.01); *A61B 34/30* (2016.02);
(Continued)

(58) Field of Classification Search
CPC .............. A61B 18/085; A61B 18/1442; A61B 18/1445; A61B 2018/00083;
(Continued)

(56) References Cited

U.S. PATENT DOCUMENTS

| | | | |
|---|---|---|---|
| 397,060 A | 1/1889 | Knapp | |
| 512,456 A | 1/1894 | John | |
(Continued)

FOREIGN PATENT DOCUMENTS

| | | | |
|---|---|---|---|
| AU | 2013254884 B2 | 9/2015 | |
| EP | 0610099 A2 | 8/1994 | |
(Continued)

OTHER PUBLICATIONS

Extended European Search Report received for European Patent Application No. 21191438.7, mailed on Dec. 16, 2021, 10 pages.
(Continued)

*Primary Examiner* — Tigist S Demie

(57) ABSTRACT

An electrosurgical instrument end effector has first and second jaw members each including an electrically conductive tissue-contacting surface. The first and second jaw members are configured to grasp and electrosurgically treat tissue between the tissue-contacting surfaces. A thermal cutting element includes a body portion extending along the tissue-contacting surface of the second jaw member and a distal probe portion extending distally therefrom. The distal probe portion extends distally beyond a distal-most extent of the second jaw member, has a free end distally-spaced from this distal-most extent, and is exposed about the entire outer periphery thereof between the distal-most extent the free
(Continued)

end. The body portion of the thermal cutting element is energizable for thermally treating tissue grasped between the tissue-contacting surfaces, while the distal probe portion of the thermal cutting element is energizable for thermally treating tissue positioned distally of the first and second jaw members.

12 Claims, 5 Drawing Sheets

(51) Int. Cl.
  *A61B 34/30* (2016.01)
  *A61B 18/00* (2006.01)
(52) U.S. Cl.
  CPC .............. *A61B 2018/00601* (2013.01); *A61B 2018/00607* (2013.01); *A61B 2018/00994* (2013.01); *A61B 2018/1452* (2013.01)
(58) Field of Classification Search
  CPC ........... A61B 2018/00107; A61B 2018/00601; A61B 2018/00607; A61B 2018/0063; A61B 2018/00994; A61B 2018/144; A61B 2018/1452; A61B 34/30
  See application file for complete search history.

(56) References Cited

U.S. PATENT DOCUMENTS

| | | | |
|---|---|---|---|
| 1,213,005 | A | 1/1917 | Pillsbury |
| 2,912,981 | A | 11/1959 | Keough |
| 2,936,760 | A | 5/1960 | Gants |
| 3,039,468 | A | 6/1962 | Price |
| 3,050,066 | A | 8/1962 | Koehn |
| 3,253,594 | A | 5/1966 | Matthews et al. |
| 3,397,699 | A | 8/1968 | Kohl |
| 3,545,443 | A | 12/1970 | Ansari |
| 3,713,447 | A | 1/1973 | Adair |
| 3,774,596 | A | 11/1973 | Cook |
| 3,800,788 | A | 4/1974 | White |
| 3,882,852 | A | 5/1975 | Sinnreich |
| 3,896,816 | A | 7/1975 | Mattler |
| 3,961,632 | A | 6/1976 | Moossun |
| RE29,207 | E | 5/1977 | Lee et al. |
| 4,083,369 | A | 4/1978 | Sinnreich |
| 4,196,734 | A | 4/1980 | Harris |
| 4,217,889 | A | 8/1980 | Radovan et al. |
| 4,243,050 | A | 1/1981 | Littleford |
| 4,276,874 | A | 7/1981 | Wolvek et al. |
| 4,312,353 | A | 1/1982 | Shahbabian |
| 4,327,709 | A | 5/1982 | Hanson et al. |
| 4,345,606 | A | 8/1982 | Littleford |
| 4,411,654 | A | 10/1983 | Boarini et al. |
| 4,416,267 | A | 11/1983 | Garren et al. |
| 4,490,137 | A | 12/1984 | Moukheibir |
| 4,493,320 | A | 1/1985 | Treat |
| 4,496,345 | A | 1/1985 | Hasson |
| 4,574,806 | A | 3/1986 | McCarthy |
| 4,581,025 | A | 4/1986 | Timmermans |
| 4,596,554 | A | 6/1986 | Dastgeer |
| 4,596,559 | A | 6/1986 | Fleischhacker |
| 4,608,965 | A | 9/1986 | Anspach, Jr. et al. |
| 4,644,936 | A | 2/1987 | Schiff |
| 4,654,030 | A | 3/1987 | Moll et al. |
| 4,685,447 | A | 8/1987 | Iversen et al. |
| 4,701,163 | A | 10/1987 | Parks |
| 4,701,587 | A | 10/1987 | Carter et al. |
| 4,738,666 | A | 4/1988 | Fuqua |
| 4,752,673 | A | 6/1988 | Krumme |
| 4,769,038 | A | 9/1988 | Bendavid et al. |
| 4,772,266 | A | 9/1988 | Groshong |
| 4,779,611 | A | 10/1988 | Grooters et al. |
| 4,784,133 | A | 11/1988 | Mackin |
| 4,793,348 | A | 12/1988 | Palmaz |
| 4,798,205 | A | 1/1989 | Bonomo et al. |
| 4,800,901 | A | 1/1989 | Rosenberg |
| 4,802,479 | A | 2/1989 | Haber et al. |
| 4,807,620 | A | 2/1989 | Strul et al. |
| 4,813,429 | A | 3/1989 | Eshel et al. |
| 4,840,613 | A | 6/1989 | Balbierz et al. |
| 4,848,337 | A | 7/1989 | Shaw et al. |
| 4,854,316 | A | 8/1989 | Davis |
| 4,860,745 | A | 8/1989 | Farin et al. |
| 4,861,334 | A | 8/1989 | Nawaz |
| 4,865,593 | A | 9/1989 | Ogawa et al. |
| 4,869,717 | A | 9/1989 | Adair |
| 4,877,944 | A | 10/1989 | Cowell et al. |
| 4,888,000 | A | 12/1989 | McQuilkin et al. |
| 4,899,747 | A | 2/1990 | Garren et al. |
| 4,905,691 | A | 3/1990 | Rydell |
| 4,914,267 | A | 4/1990 | Derbyshire |
| 4,917,668 | A | 4/1990 | Haindl |
| 4,931,042 | A | 6/1990 | Holmes et al. |
| 4,938,761 | A | 7/1990 | Ensslin |
| 4,955,895 | A | 9/1990 | Sugiyama et al. |
| 5,002,557 | A | 3/1991 | Hasson |
| 5,003,991 | A | 4/1991 | Takayama et al. |
| 5,009,643 | A | 4/1991 | Reich et al. |
| 5,030,206 | A | 7/1991 | Lander |
| 5,030,227 | A | 7/1991 | Rosenbluth et al. |
| 5,047,025 | A | 9/1991 | Taylor et al. |
| 5,074,871 | A | 12/1991 | Groshong |
| 5,087,804 | A | 2/1992 | McGaffigan |
| 5,098,392 | A | 3/1992 | Fleischhacker et al. |
| 5,104,383 | A | 4/1992 | Shichman |
| 5,116,318 | A | 5/1992 | Hillstead |
| 5,116,357 | A | 5/1992 | Eberbach |
| 5,122,122 | A | 6/1992 | Allgood |
| 5,122,155 | A | 6/1992 | Eberbach |
| 5,137,512 | A | 8/1992 | Burns et al. |
| 5,141,494 | A | 8/1992 | Danforth et al. |
| 5,141,515 | A | 8/1992 | Eberbach |
| 5,147,316 | A | 9/1992 | Castillenti |
| 5,147,374 | A | 9/1992 | Fernandez |
| 5,158,545 | A | 10/1992 | Trudell et al. |
| 5,159,925 | A | 11/1992 | Neuwirth et al. |
| 5,163,949 | A | 11/1992 | Bonutti |
| 5,176,692 | A | 1/1993 | Wilk et al. |
| 5,176,697 | A | 1/1993 | Hasson et al. |
| 5,182,427 | A | 1/1993 | McGaffigan |
| 5,183,463 | A | 2/1993 | Debbas |
| 5,188,596 | A | 2/1993 | Condon et al. |
| 5,188,630 | A | 2/1993 | Christoudias |
| 5,189,271 | A | 2/1993 | Derbyshire |
| 5,195,507 | A | 3/1993 | Bilweis |
| 5,201,742 | A | 4/1993 | Hasson |
| 5,201,754 | A | 4/1993 | Crittenden et al. |
| 5,209,725 | A | 5/1993 | Roth |
| 5,215,526 | A | 6/1993 | Deniega et al. |
| 5,222,970 | A | 6/1993 | Reeves |
| 5,226,890 | A | 7/1993 | Ianniruberto et al. |
| 5,232,446 | A | 8/1993 | Arney |
| 5,232,451 | A | 8/1993 | Freitas et al. |
| 5,234,454 | A | 8/1993 | Bangs |
| 5,250,025 | A | 10/1993 | Sosnowski et al. |
| 5,250,046 | A | 10/1993 | Lee |
| 5,258,026 | A | 11/1993 | Johnson et al. |
| 5,269,753 | A | 12/1993 | Wilk |
| 5,290,249 | A | 3/1994 | Foster et al. |
| 5,300,068 | A | 4/1994 | Rosar et al. |
| 5,300,750 | A | 4/1994 | Carter, Jr. et al. |
| 5,308,311 | A | 5/1994 | Eggers et al. |
| 5,308,327 | A | 5/1994 | Heaven et al. |
| 5,314,443 | A | 5/1994 | Rudnick |
| 5,318,012 | A | 6/1994 | Wilk |
| 5,330,497 | A | 7/1994 | Freitas et al. |
| 5,337,733 | A | 8/1994 | Bauerfeind et al. |
| 5,342,307 | A | 8/1994 | Euteneuer et al. |
| 5,346,504 | A | 9/1994 | Ortiz et al. |
| 5,359,995 | A | 11/1994 | Sewell, Jr. |
| 5,370,134 | A | 12/1994 | Chin et al. |
| 5,383,889 | A | 1/1995 | Warner et al. |

(56)                References Cited

U.S. PATENT DOCUMENTS

| | | | |
|---|---|---|---|
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,514,153 A | 5/1996 | Bonutti | |
| 5,540,658 A | 7/1996 | Evans et al. | |
| 5,540,679 A | 7/1996 | Fram et al. | |
| 5,540,711 A | 7/1996 | Kieturakis et al. | |
| 5,607,443 A | 3/1997 | Kieturakis et al. | |
| 5,628,771 A | 5/1997 | Mizukawa et al. | |
| 5,656,013 A | 8/1997 | Yoon | |
| 5,667,520 A | 9/1997 | Bonutti | |
| 5,704,372 A | 1/1998 | Moll et al. | |
| 5,707,369 A | 1/1998 | Vaitekunas et al. | |
| 5,707,382 A | 1/1998 | Sierocuk et al. | |
| 5,707,402 A | 1/1998 | Heim | |
| 5,713,869 A | 2/1998 | Morejon | |
| 5,722,986 A | 3/1998 | Smith et al. | |
| 5,730,756 A | 3/1998 | Kieturakis et al. | |
| 5,738,628 A | 4/1998 | Sierocuk et al. | |
| 5,755,693 A | 5/1998 | Walker et al. | |
| 5,762,604 A | 6/1998 | Kieturakis | |
| 5,772,680 A | 6/1998 | Kieturakis et al. | |
| 5,779,728 A | 7/1998 | Lunsford et al. | |
| 5,797,947 A | 8/1998 | Mollenauer | |
| 5,803,901 A | 9/1998 | Chin et al. | |
| 5,807,392 A | 9/1998 | Eggers | |
| 5,810,867 A | 9/1998 | Zarbatany et al. | |
| 5,827,271 A | 10/1998 | Buysse et al. | |
| 5,836,913 A | 11/1998 | Orth et al. | |
| 5,865,802 A | 2/1999 | Yoon et al. | |
| 5,876,401 A | 3/1999 | Schulze et al. | |
| 5,893,866 A | 4/1999 | Hermann et al. | |
| 5,911,719 A | 6/1999 | Eggers | |
| 5,925,058 A | 7/1999 | Smith et al. | |
| 6,086,586 A | 7/2000 | Hooven | |
| 6,221,039 B1 | 4/2001 | Durgin et al. | |
| 6,235,027 B1 | 5/2001 | Herzon | |
| 6,273,887 B1 | 8/2001 | Yamauchi et al. | |
| 6,361,543 B1 | 3/2002 | Chin et al. | |
| 6,375,665 B1 | 4/2002 | Nash et al. | |
| 6,379,372 B1 | 4/2002 | Dehdashtian et al. | |
| 6,432,121 B1 | 8/2002 | Jervis | |
| 6,447,529 B2 | 9/2002 | Fogarty et al. | |
| 6,468,205 B1 | 10/2002 | Mollenauer et al. | |
| 6,506,200 B1 | 1/2003 | Chin | |
| 6,514,272 B1 | 2/2003 | Kieturakis et al. | |
| 6,517,514 B1 | 2/2003 | Campbell | |
| 6,527,787 B1 | 3/2003 | Fogarty et al. | |
| 6,540,764 B1 | 4/2003 | Kieturakis et al. | |
| 6,602,252 B2 | 8/2003 | Mollenauer | |
| 6,626,901 B1 | 9/2003 | Treat et al. | |
| 6,692,489 B1 | 2/2004 | Heim et al. | |
| 6,726,683 B1 | 4/2004 | Shaw | |
| 6,736,813 B2 | 5/2004 | Yamauchi et al. | |
| 6,776,780 B2 | 8/2004 | Mulier et al. | |
| 6,796,960 B2 | 9/2004 | Cioanta et al. | |
| 6,802,843 B2 | 10/2004 | Truckai et al. | |
| 6,808,525 B2 | 10/2004 | Latterell et al. | |
| 6,860,880 B2 | 3/2005 | Treat et al. | |
| 6,929,641 B2 | 8/2005 | Goble et al. | |
| 7,011,656 B2 | 3/2006 | McGaffigan et al. | |
| 7,025,065 B2 | 4/2006 | McGaffigan et al. | |
| 7,033,356 B2 | 4/2006 | Latterell et al. | |
| 7,070,597 B2 | 7/2006 | Truckai et al. | |
| 7,083,619 B2 | 8/2006 | Truckai et al. | |
| 7,112,201 B2 | 9/2006 | Truckai et al. | |
| 7,125,409 B2 | 10/2006 | Truckai et al. | |
| 7,147,637 B2 | 12/2006 | Goble | |
| 7,169,146 B2 | 1/2007 | Truckai et al. | |
| 7,204,835 B2 | 4/2007 | Latterell et al. | |
| 7,211,079 B2 | 5/2007 | Treat | |
| 7,270,664 B2 | 9/2007 | Johnson et al. | |
| 7,276,068 B2 | 10/2007 | Johnson et al. | |
| 7,326,202 B2 | 2/2008 | McGaffigan | |
| 7,329,255 B2 | 2/2008 | McGaffigan | |
| 7,354,440 B2 | 4/2008 | Truckal et al. | |
| 7,357,802 B2 | 4/2008 | Palanker et al. | |
| 7,815,641 B2 | 10/2010 | Dodde et al. | |
| 7,931,649 B2 | 4/2011 | Couture et al. | |
| 7,972,334 B2 | 7/2011 | McGreevy et al. | |
| 8,034,051 B2 | 10/2011 | Martin et al. | |
| 8,187,273 B2 | 5/2012 | Kerr et al. | |
| 8,197,472 B2 | 6/2012 | Lau et al. | |
| 8,292,879 B2 | 10/2012 | Manwaring et al. | |
| 8,382,748 B2 | 2/2013 | Geisel | |
| 8,394,094 B2 | 3/2013 | Edwards et al. | |
| 8,454,645 B2 | 6/2013 | Criscuolo et al. | |
| 8,480,666 B2 | 7/2013 | Buysse et al. | |
| 8,491,626 B2 | 7/2013 | Roy et al. | |
| 8,551,088 B2 | 10/2013 | Falkenstein et al. | |
| 8,568,410 B2 | 10/2013 | Vakharia et al. | |
| 8,597,297 B2 | 12/2013 | Couture et al. | |
| 8,617,151 B2 | 12/2013 | Denis et al. | |
| 8,623,003 B2 | 1/2014 | Lau et al. | |
| 8,679,115 B2 | 3/2014 | Reschke | |
| 8,734,445 B2 | 5/2014 | Johnson et al. | |
| 8,915,909 B2 | 12/2014 | Manwaring et al. | |
| 8,932,279 B2 | 1/2015 | Stringham et al. | |
| 8,951,248 B2 | 2/2015 | Messerly et al. | |
| 8,968,305 B2 | 3/2015 | Dumbauld et al. | |
| 9,005,199 B2 | 4/2015 | Beckman et al. | |
| 9,039,694 B2 | 5/2015 | Ross et al. | |
| 9,050,100 B2 | 6/2015 | Yates et al. | |
| 9,084,606 B2 | 7/2015 | Greep | |
| 9,131,977 B2 | 9/2015 | Manwaring et al. | |
| 9,192,427 B2 | 11/2015 | Johnson et al. | |
| 9,265,556 B2 | 2/2016 | Manwaring et al. | |
| 9,387,037 B2 | 7/2016 | Yang | |
| 9,402,679 B2 | 8/2016 | Ginnebaugh et al. | |
| 9,918,774 B2 | 3/2018 | Batchelor et al. | |
| 9,931,157 B2 | 4/2018 | Strobl et al. | |
| 9,955,858 B2 | 5/2018 | Pamnani et al. | |
| 10,204,773 B2 | 2/2019 | Sugiyama et al. | |
| 10,213,247 B2 | 2/2019 | Manwaring et al. | |
| 2002/0107517 A1 | 8/2002 | Witt et al. | |
| 2003/0040744 A1 | 2/2003 | Latterell et al. | |
| 2003/0130658 A1 | 7/2003 | Goble et al. | |
| 2003/0144660 A1 | 7/2003 | Mollenauer | |
| 2003/0171747 A1 | 9/2003 | Kanehira et al. | |
| 2004/0030330 A1 | 2/2004 | Brassell et al. | |
| 2004/0049185 A1 | 3/2004 | Latterell et al. | |
| 2004/0167506 A1 | 8/2004 | Chen | |
| 2004/0176756 A1 | 9/2004 | McGaffigan | |
| 2005/0107776 A1 | 5/2005 | McGaffigan et al. | |
| 2005/0192633 A1 | 9/2005 | Montpetit | |
| 2006/0212030 A1 | 9/2006 | McGaffigan | |
| 2006/0217706 A1 | 9/2006 | Lau et al. | |
| 2007/0074807 A1 | 4/2007 | Guerra | |
| 2007/0156137 A1 | 7/2007 | Geisel | |
| 2007/0270924 A1 | 11/2007 | McCann et al. | |
| 2008/0091170 A1 | 4/2008 | Vargas et al. | |
| 2009/0248002 A1 | 10/2009 | Takashino et al. | |
| 2009/0254081 A1 | 10/2009 | Allison et al. | |
| 2010/0152725 A1 | 6/2010 | Pearson et al. | |
| 2010/0198216 A1 | 8/2010 | Palanker | |
| 2010/0268211 A1 | 10/2010 | Manwaring et al. | |
| 2011/0028964 A1 | 2/2011 | Edwards | |
| 2011/0077629 A1 | 3/2011 | Tanaka et al. | |
| 2012/0059374 A1* | 3/2012 | Johnson | A61B 18/1445 |
| | | | 606/48 |
| 2012/0226270 A1 | 9/2012 | Manwaring et al. | |
| 2012/0330295 A1 | 12/2012 | Manwaring et al. | |
| 2013/0012934 A1 | 1/2013 | Manwaring et al. | |
| 2013/0018411 A1 | 1/2013 | Collings et al. | |
| 2013/0046303 A1 | 2/2013 | Evans et al. | |
| 2013/0046337 A1 | 2/2013 | Evans et al. | |
| 2013/0066310 A1 | 3/2013 | Manwaring et al. | |
| 2013/0123837 A1 | 5/2013 | Roy et al. | |
| 2014/0135804 A1 | 5/2014 | Weisenburgh et al. | |
| 2014/0194875 A1 | 7/2014 | Reschke et al. | |
| 2014/0276796 A1 | 9/2014 | Batchelor et al. | |
| 2015/0018825 A1 | 1/2015 | Takashino | |

(56)　　　References Cited

U.S. PATENT DOCUMENTS

| | | |
|---|---|---|
| 2015/0032094 A1 | 1/2015 | Kane et al. |
| 2015/0051598 A1 | 2/2015 | Orszulak et al. |
| 2015/0088128 A1 | 3/2015 | Couture |
| 2015/0216589 A1 | 8/2015 | Wittenberger et al. |
| 2015/0320485 A1 | 11/2015 | Batchelor et al. |
| 2016/0249975 A1* | 9/2016 | Konishi ............. A61B 18/1445 |
| | | 606/45 |
| 2017/0196648 A1 | 7/2017 | Ward et al. |
| 2017/0252087 A1 | 9/2017 | Takashino et al. |
| 2018/0092661 A1 | 4/2018 | Prabhu |
| 2018/0206905 A1 | 7/2018 | Batchelor et al. |
| 2018/0280084 A1 | 10/2018 | Hancock et al. |
| 2019/0000538 A1 | 1/2019 | Widenhouse et al. |
| 2019/0321591 A1 | 10/2019 | Rogers |
| 2020/0178763 A1 | 6/2020 | Tilson et al. |
| 2020/0237423 A1 | 7/2020 | Witte et al. |
| 2021/0022798 A1* | 1/2021 | Hammerland, III ......................... |
| | | A61B 18/1442 |
| 2023/0310063 A1 | 10/2023 | Allen, IV et al. |

FOREIGN PATENT DOCUMENTS

| | | | |
|---|---|---|---|
| EP | 0880939 | A1 | 12/1998 |
| EP | 2679176 | A1 | 1/2014 |
| EP | 3034023 | A1 | 6/2016 |
| WO | 9206638 | A1 | 4/1992 |
| WO | 9218056 | A1 | 10/1992 |
| WO | 9309722 | A1 | 5/1993 |
| WO | 9912602 | A1 | 3/1999 |
| WO | 0126724 | A2 | 4/2001 |
| WO | 02096307 | A2 | 12/2002 |
| WO | 2015094493 | A1 | 6/2015 |
| WO | 2018022813 | A1 | 2/2018 |
| WO | 2020018934 | A1 | 1/2020 |

OTHER PUBLICATIONS

International Preliminary Report on Patentability received for PCT Patent Application No. PCT/US2021/048658, mailed on Mar. 16, 2023, 10 pages.

International Search Report and Written Opinion received for PCT Patent Application No. PCT/US2021/045549, mailed on Jan. 5, 2022, 10 pages.

International Search Report and Written Opinion received for PCT Patent Application No. PCT/US2021/048658, mailed on Dec. 10, 2021, 14 pages.

Non-Final Office Action received for U.S. Appl. No. 18/023,799, mailed on Jun. 16, 2025, 8 pages.

Final Office Action received for U.S. Appl. No. 18/023,799, mailed on Sep. 30, 2025, 10 pages.

Non-Final Office Action received for U.S. Appl. No. 18/023,799, mailed on Feb. 17, 2026, 12 pages.

* cited by examiner

ELECTROSURGICAL INSTRUMENTS, SYSTEMS, AND METHODS INCLUDING USE OF THERMAL CUTTING ELEMENTS

CROSS-REFERENCE TO RELATED APPLICATIONS

This application is a 371 National Stage Application of International Application No. PCT/US2021/045549, filed Aug. 11, 2021, which claims the benefit of U.S. Provisional Patent Application No. 63/072,784, filed Aug. 31, 2020, the entire contents of each of which are hereby incorporated herein by reference.

FIELD

The present disclosure relates to electrosurgical instruments, systems, and methods and, more particularly, to thermal cutting elements for use in electrosurgical instruments, system, and methods to facilitate tissue treatment, e.g., sealing, cutting, and/or coagulation of tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is farther from an operator (whether a human surgeon or a surgical robotic), while the term "proximal" refers to the portion that is being described which is closer to the operator. Terms including "generally," "about," "substantially," and the like, as utilized herein, are meant to encompass variations up to and including plus or minus 10 percent to take into account, for example, material, measurement, manufacturing, environmental, use, and/or other tolerances and variations. Further, to the extent consistent, any or all of the aspects detailed herein may be used in conjunction with any or all of the other aspects detailed herein.

Provided in accordance with aspects of the present disclosure is an electrosurgical instrument including an end effector assembly having first and second jaw members each including an electrically conductive tissue-contacting surface. At least one of the first or second jaw members is movable relative to the other from a spaced-apart position to an approximated position to grasp tissue between the tissue-contacting surfaces. The first and second jaw members are adapted to connect to a source of energy for electrosurgically treating tissue grasped between the tissue-contacting surfaces. A thermal cutting element has a body portion extending along at least a portion of a length of the tissue-contacting surface of the second jaw member and a distal probe portion extending distally from the body portion. The distal probe portion, more specifically, extends distally beyond a distal-most extent of the second jaw member such that a free end of the distal probe is distally-spaced from the distal-most extent of the second jaw member. The distal probe portion is exposed about the entire outer periphery thereof along a length defined between the distal-most extent of the second jaw member and the free end of the distal probe portion. The body portion of the thermal cutting element is adapted to connect to a source of energy for thermally treating tissue grasped between the tissue-contacting surfaces, and the distal probe portion of the thermal cutting element adapted to connect to a source of energy for thermally treating tissue positioned distally of the first and second jaw members.

In an aspect of the present disclosure, the tissue-contacting surfaces of the first and second jaw members are configured to conduct RF energy therebetween and through tissue to seal tissue grasped between the tissue-contacting surfaces.

In another aspect of the present disclosure, the thermal cutting element is a ferromagnetic cutting element, e.g., a ferromagnetic cutting wire. The ferromagnetic cutting element may provide automatic Curie temperature control upon supply of energy thereto.

In yet another aspect of the present disclosure, the thermal cutting element includes a substrate including a heating layer disposed on at least a portion of the substrate. The substrate may be at least partially Plasma Electrolytic Oxidation (PEO)-treated. Further, the thermal cutting element may be configured to establish a thermal gradient to conduct heat from portions of the thermal cutting element not in contact with tissue to portions of the thermal cutting element in contact with tissue.

In still another aspect of the present disclosure, the body portion of the thermal cutting element and the distal probe portion of the thermal cutting element are collectively activatable. Alternatively, the body portion of the thermal cutting element and the distal probe portion of the thermal cutting element are independently activatable.

In still yet another aspect of the present disclosure, the electrosurgical instrument further includes a housing having a shaft extending distally therefrom, wherein the end effector assembly is disposed at a distal end of the shaft.

In another aspect of the present disclosure, the end effector is adapted to connect to an arm of a robotic surgical system.

In another aspect of the present disclosure, the electrosurgical instrument further includes first and second shafts coupled to one another about a pivot, wherein the end effector assembly is disposed at distal ends of the first and second shafts.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
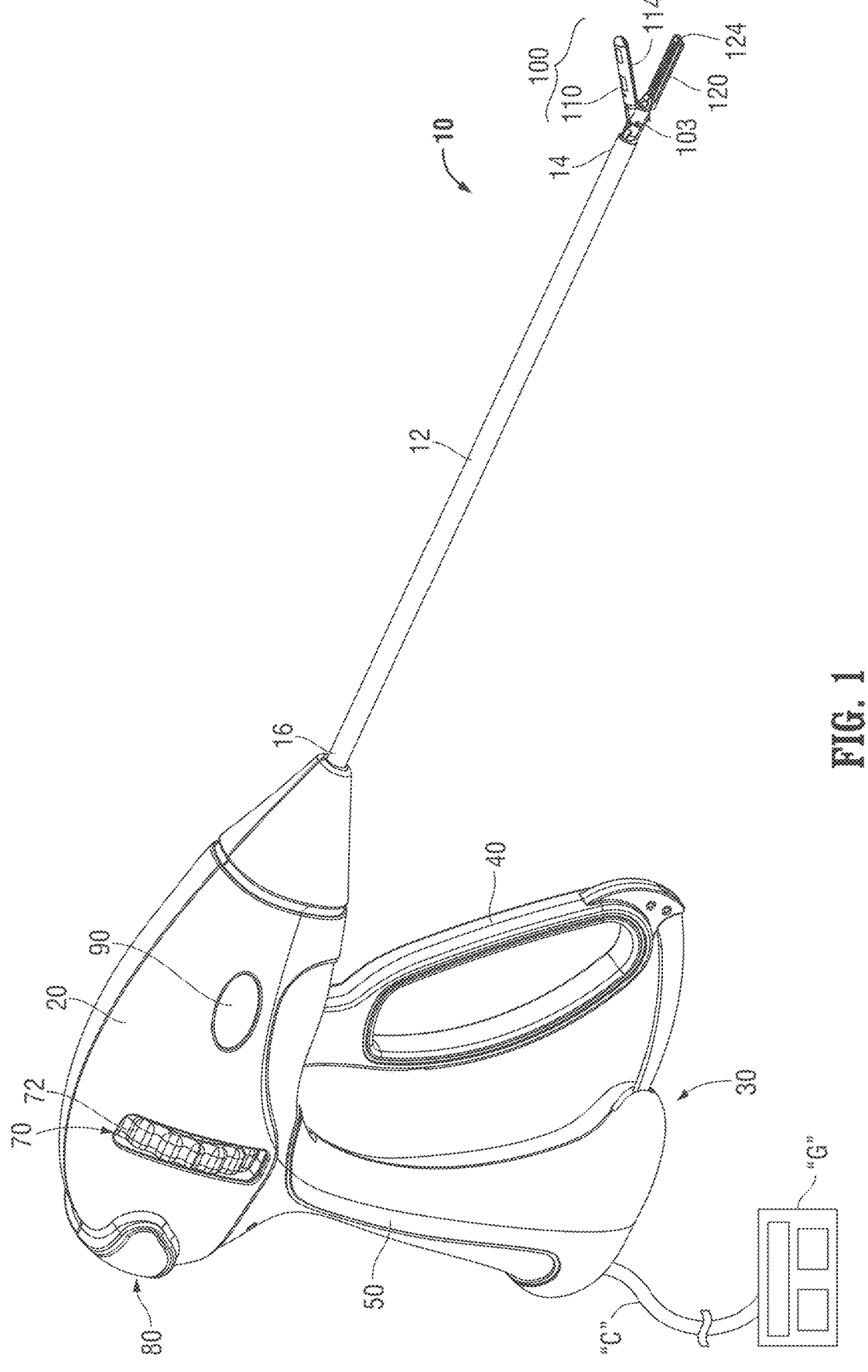
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., a generator "G." Cable "C" includes a wire (or wires) (not shown) extending therethrough that has sufficient length to extend through shaft 12 in order to connect to one or both tissue-treating surfaces 114, 124 of jaw members 110, 120, respectively, and thermal cutting element 130 of end effector assembly 100 (see FIG. 4) to provide energy thereto. More specifically, first activation switch 80 is coupled to tissue-treating surfaces 114, 124 (FIG. 4) and the generator "G" for enabling the selective activation of the supply of energy to jaw members 110, 120 for electrosurgically treating, e.g., sealing, tissue. Second activation switch 90 is coupled to thermal cutting element 130 of jaw member 120 (FIG. 4) and the generator "G" for enabling the selective activation of the supply of energy to thermal cutting element 130 for thermally treating, e.g., cutting and/or coagulating, tissue.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly 60 (FIG. 4) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110,

4

120. Rotating assembly 70 includes a rotation wheel 72 that is selectively rotatable in either direction to correspondingly rotate end effector assembly 100 relative to housing 20.

Figure 2:
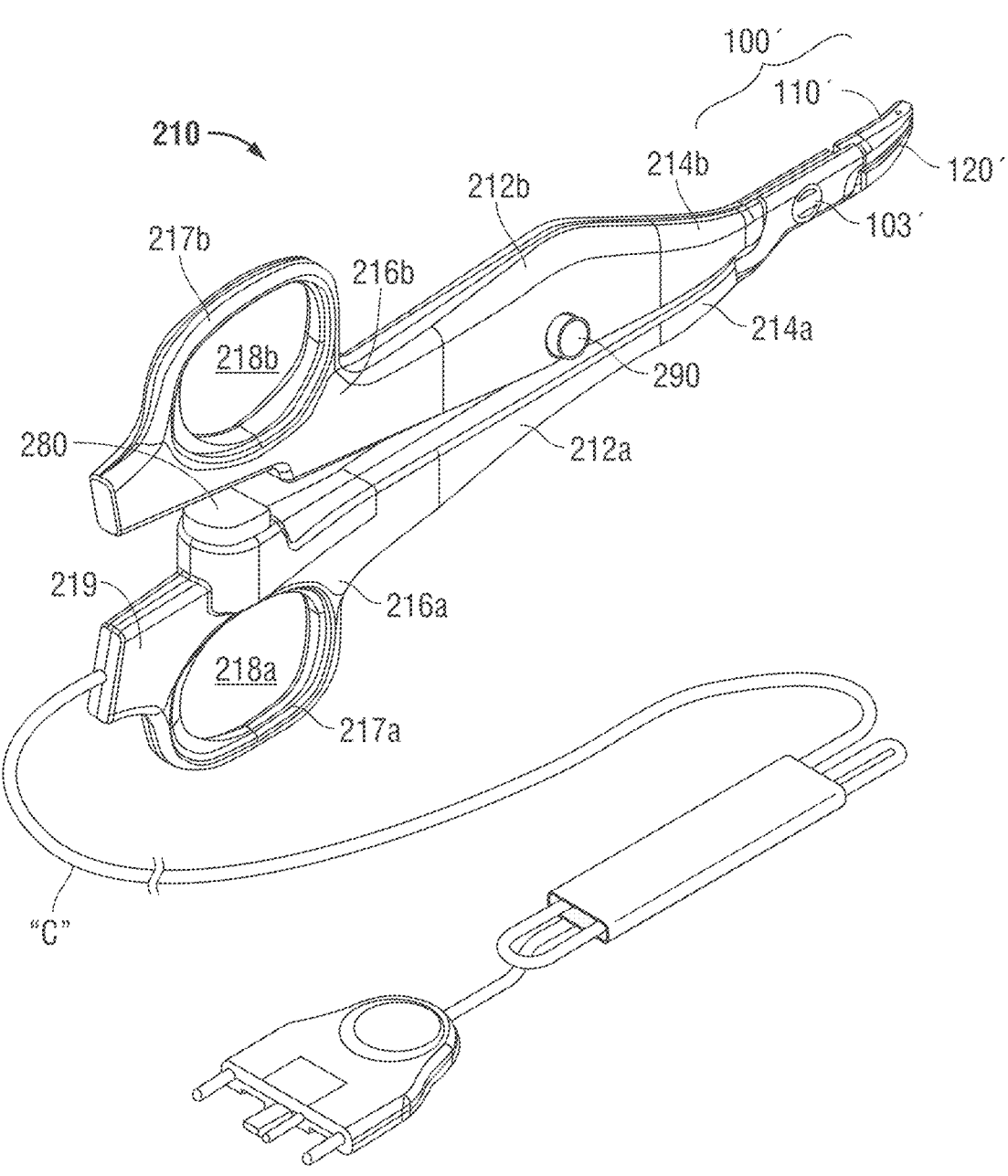
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
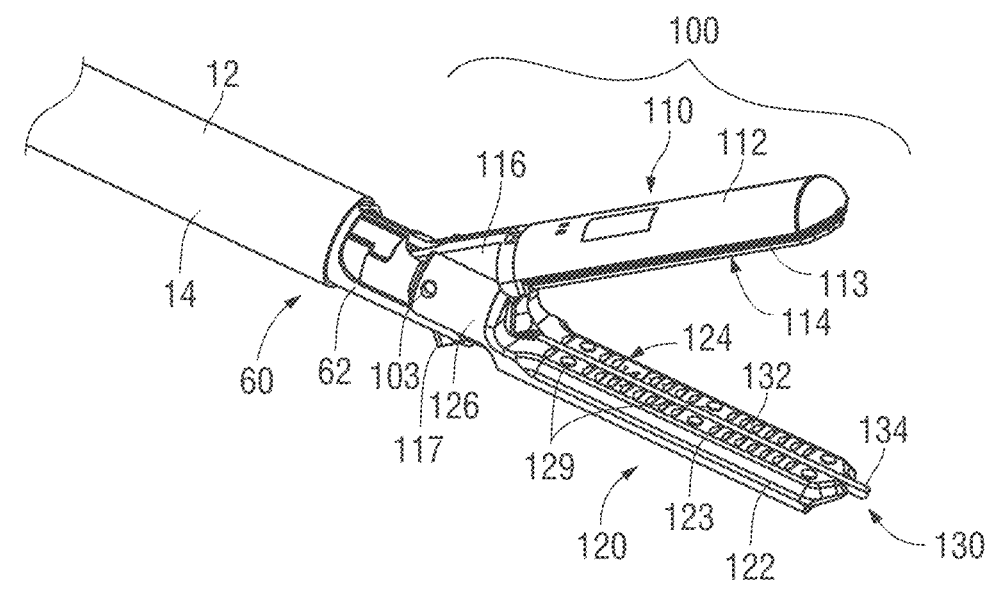
FIG. 4 is a perspective view of an end effector assembly configured for use with the shaft-based electrosurgical forceps of FIG. 1, the hemostat-style electrosurgical forceps of FIG. 2, the robotic surgical instrument of FIG. 3, or any other suitable surgical instrument.

Forceps 210 includes two elongated shaft members 212a, 212b, each having a proximal end portion 216a, 216b, and a distal end portion 214a, 214b, respectively. Forceps 210 is configured for use with an end effector assembly 100' similar to end effector assembly 100 (FIG. 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212b, includes a proximal shaft connector 219 configured to connect forceps 210 to a source of energy, e.g., generator "G" (FIG. 1). Proximal shaft connector 219 secures a cable "C" to forceps 210 such that the user may selectively supply energy to jaw members 110', 120' and a thermal cutting element (not shown, similar to thermal cutting element 130 of jaw member 120 (FIG. 4)) of end effector assembly 100' for treating tissue. More specifically, a first activation switch 280 is provided for supplying energy to jaw members 110', 120' to electrosurgically treat tissue upon sufficient approximation of shaft members 212a, 212b, e.g., upon activation of first activation switch 280 via shaft member 212a. A second activation switch 290 disposed on either or both of shaft members 212a, 212b is coupled to the thermal cutting element of end effector assembly 100' and to generator "G" for enabling the selective activation of the supply of energy to the thermal cutting element for thermally treating tissue.

Jaw members 110', 120' define a curved configuration wherein each jaw member is similarly curved laterally off of a longitudinal axis of end effector assembly 100'. However, other suitable curved configurations including curvature towards one of the jaw members 110, 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
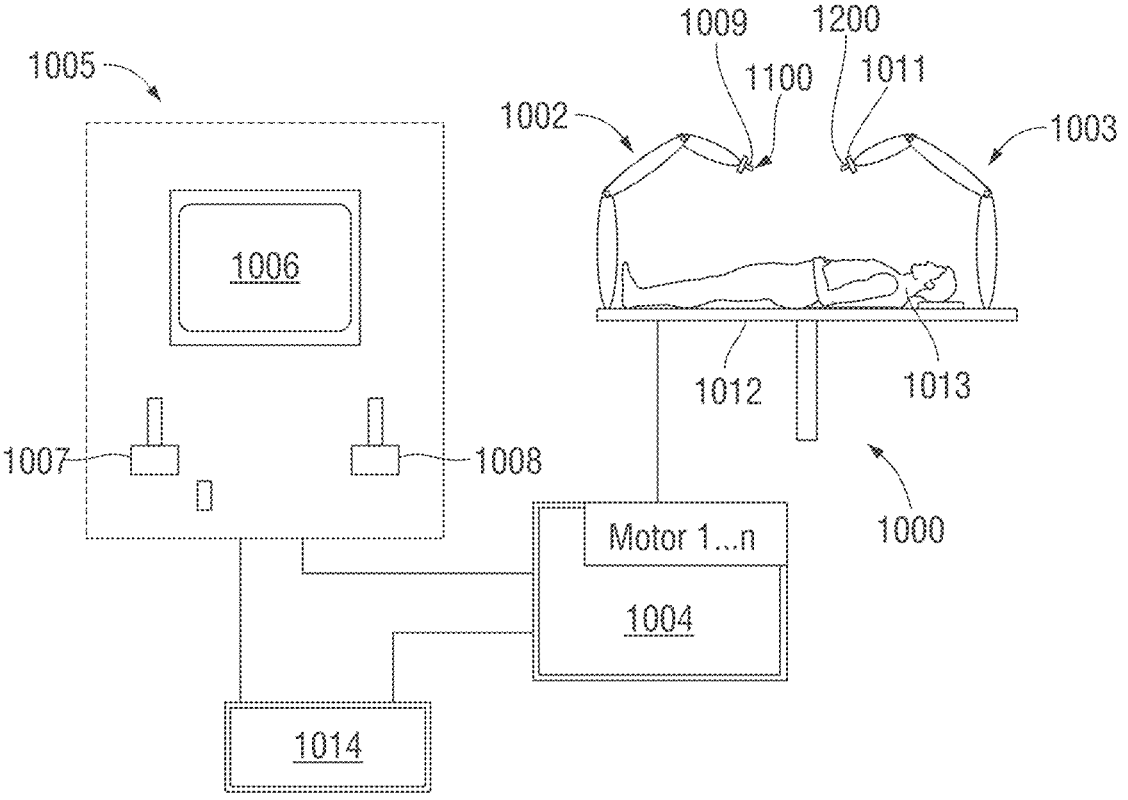
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached (directly or indirectly via intermediate structures, e.g., a housing and shaft extending from the housing), for example, an end effector assembly 1100, 1200, respectively. End effector assembly 1100 is similar to end effector assembly 100 (FIG. 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
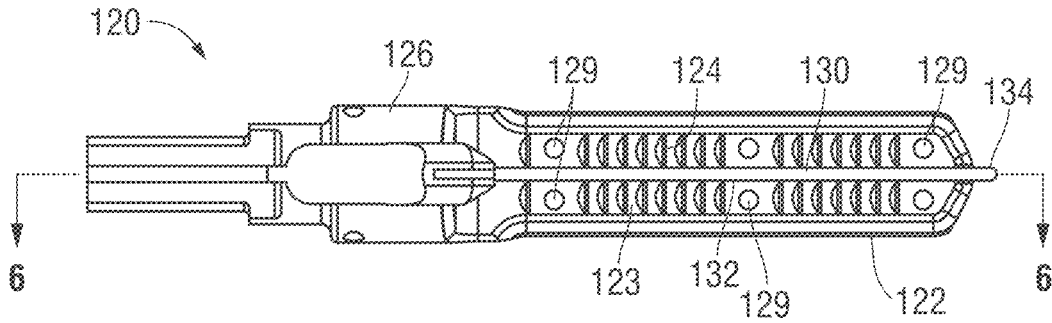
FIG. 5 is a top view of a jaw member of the end effector assembly of FIG. 4.
Figure 6:
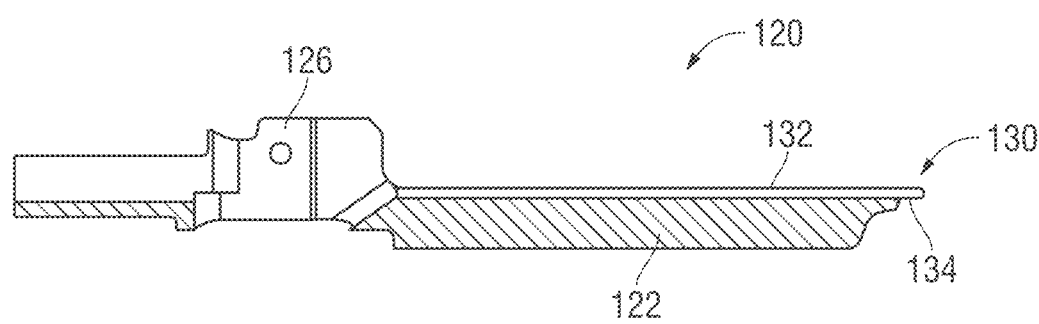
FIG. 6 is a longitudinal, cross-sectional view taken across section line "6-6" of FIG. 5.

Turning to FIGS. 4-6, end effector assembly 100, as noted above, includes first and second jaw members 110, 120. Each jaw member 110, 120 may include a structural frame 111, 121, a jaw body 112, 122, and a tissue-treating plate 113, 123 defining the respective tissue-treating surface 114, 124 thereof, although other configurations of either or both of jaw members 110, 120 (including different configurations for each jaw member 110, 120) are also contemplated.

Structural frames 111, 121 provide structural support to jaw members 110, 120 and include proximal flange portions 116, 126 that are operably coupled to one another and/or shaft 12 to enable pivoting of one or both of jaw members 110, 120 relative to the other (and shaft 12) between the spaced-apart position and the approximated position for grasping tissue between tissue-treating surfaces 114, 124. More specifically, proximal flange portion 126 may be bifurcated to define a pair of spaced-apart proximal flange portion segments that receive proximal flange portion 116 of jaw member 110 therebetween with pivot 103 extending through aligned apertures defined within the proximal flange portion segments of proximal flange portion 126 and proximal flange portion 116 to pivotably couple jaw members 110, 120 with one another. Proximal flange portion 116 may further include at least one protrusion 117 extending therefrom that is configured for receipt within an aperture defined within a drive sleeve 62 of drive assembly 60 such that translation of drive sleeve 62, e.g., in response to actuation of movable handle 40 (FIG. 1) or a robotic drive, pivots jaw member 110 about pivot 103 and relative to jaw member 120 between the spaced-apart position and the approximated position. However, other suitable drive arrangements are also contemplated, e.g., using cam pins and cam slots, a screw-drive mechanism, etc.

Jaw bodies 112, 122 at least partially surround, support, and/or retain the components of the corresponding jaw members 110, 120, e.g., structural frames 111, 121 and tissue-treating plates 113, 123. Jaw bodies 112, 122 may be formed from electrically and thermally insulative material(s) and may each be formed from a single, monolithic component or from multiple components. For example, jaw bodies 112, 122 may include outer jaw housings and inner jaw inserts, one or both of which is formed via overmolding onto jaw members 110, 120. Alternatively, some or all of the component(s) of jaw bodies 112, 122 may be separately formed and subsequently assembled with jaw members 110, 120.

In some configurations, tissue-treating plates 113, 123 may be deposited onto jaw bodies 112, 122, e.g., via sputtering or other deposition techniques. Alternatively, tissue-treating plates 113, 123 may be pre-formed and engaged with jaw bodies 112, 122 via, for example, overmolding, adhesion, mechanical engagement, etc. Lead wires (not shown) or other suitable electrical connecting structures are connected to tissue-treating plates 113, 123 to connect tissue-treating plates 113, 123 to generator "G" (FIG. 1) and/or first activation switch 80 (FIG. 1). More specifically, tissue-treating plates 113, 123 are formed from electrically conductive material(s), e.g., for conducting RF electrosurgical energy therebetween for electrosurgically treating tissue, although tissue-treating plates 113, 123 may alternatively be configured to conduct any other suitable energy, e.g., thermal, microwave, light, ultrasonic, etc., to or through tissue grasped therebetween for energy-based tissue treatment. With respect to RF electrosurgical energy configurations, tissue-treating plates 113, 123 may be energized to different potentials to establish a potential gradient for conducting energy through tissue disposed therebetween, e.g., to seal or otherwise electrosurgically treat the tissue. One or more stops 129 configured to inhibit shorting between tissue-treating plates 113, 123 may be disposed on either or both tissue-treating plates 113, 123.

With reference to FIGS. 5 and 6, jaw member 120, as noted above, includes structural frame 121, jaw body 122, and tissue-treating plate 123 defining tissue-treating surface 124 thereof. Jaw member 120 further includes thermal cutting element 130 disposed thereon or therein. Thermal cutting element 130 includes a body portion 132 that extends longitudinally along tissue-treating plate 123 and may be disposed within a longitudinally-extending slot 125 defined through tissue-treating plate 123 and/or a portion of jaw body 122. Alternatively, thermal cutting element 130 may be disposed on tissue-treating plate 123 with or without an insulating layer(s) disposed therebetween. At least a portion of the body portion 132 of tissue-contacting surface of thermal cutting element 130 may be substantially co-planar with tissue-treating surface 124, may be recessed relative thereto, and/or may protrude therefrom. As body portion 132 of thermal cutting element 130 extends between opposing portions of tissue-treating plate 123, body portion 132 may thus be utilized to cut sealed (or otherwise treated) tissue into two sealed tissue portions. This enables a surgeon, for example, to safely and effectively seal and divide a vessel, lumen, or other tissue. Thermal cutting element 130 is selectively energizable to enable body portion 132 thereof to thermally treat, e.g., cut, tissue grasped between tissue-treating plates 113, 123 (see also FIG. 4). Lead wires (not shown) or other suitable electrical connecting structures are connected to thermal cutting element 130 to connect thermal cutting element 130 to generator "G" (FIG. 1) and/or second activation switch 90 (FIG. 1).

A distal probe portion 134 of thermal cutting element 130 extends distally beyond a distal edge of tissue-treating plate 123 and a distal-most extent of jaw body 122. Distal probe portion 134 is selectively energizable together with or independently of body portion 132 to thermally treat tissue disposed distally of jaw bodies 112, 122 and/or tissue-treating plates 113, 123 (see also FIG. 4). Distal probe portion 134 may define any suitable configuration, e.g., linear, curved, angled, irregular, bulbous, geometric, combinations thereof, etc. Distal probe portion 134 defines a cantilever configuration wherein a free end of distal probe portion 134 is distally-spaced from the distal edge of tissue-treating plate 123 and the distal-most extent of jaw body 122 and wherein a length of distal probe portion 134 extending from the distal edge of tissue-treating plate 123 and/or the distal-most extent of jaw body 122 is exposed about the entire outer periphery thereof. In this manner, distal probe portion 134 may be urged into contact with tissue, moved along tissue, plunged into tissue, etc. without the distal edge of tissue-treating plate 123 and/or the distal-most extent of jaw body 122 contacting, moving along, plunging into, etc. tissue. As such, distal probe portion 134 may be used for backscoring, spot coagulation, cauterization, tissue dissection, plunging into tissue, creating holes or perforations in tissue, performing enterotomies, cutting tissue via tenting, other thermal tissue treatments, etc.

Referring again to FIGS. 4, in the approximated position of jaw members 110, 120, the free end of distal probe portion 134 is also distally-spaced from the distal edge of tissue-treating plate 113 and the distal-most extent of jaw body 112 to provide the above-noted functionality with the jaw members 110, 120 disposed in either the spaced-apart position or the approximated position. Further, in addition to extending distally beyond jaw member 110 and the other components of jaw member 120, distal probe portion 134 extends distally beyond the electrosurgical tissue treatment zone associated with jaw members 110, 120; that is, distal probe portion 134 extend distally beyond the volume within which tissue may be electrosurgically treated, e.g., sealed, via tissue-treating plates 113, 123. However, as distal probe portion 134 provides the ability to coagulate tissue in addition to cutting tissue, bleeding of tissue cut by distal probe portion 134 outside the electrosurgical tissue treatment zone, e.g., tissue that has not been sealed, can be effectively controlled.

Figure 7:
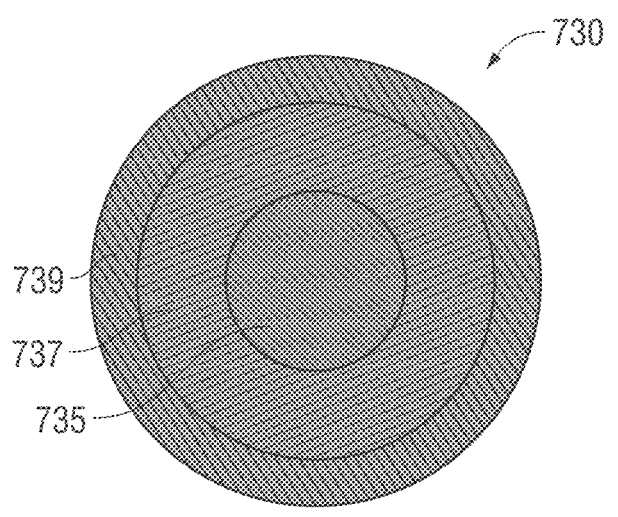
FIG. 7 is a transverse, cross-sectional view of a thermal cutting element configured for use with the end effector assembly of FIG. 4.

Turning to FIG. 7, thermal cutting element 130 (FIGS. 4-6) may be any suitable thermal cutting element such as, for example, a thermal cutting wire 730 configured as a ferromagnetic thermal cutting wire including a solid conductive core 735 and one or more layers of ferromagnetic coating 737, 739 disposed about solid conductive core 735. More specifically, ferromagnetic thermal cutting wire 730 includes solid conductive core 735, e.g., copper, inner ferromagnetic coating 737 disposed about solid conductive core 735, and outer ferromagnetic coating 739 disposed about inner ferromagnetic coating 737. Inner and outer ferromagnetic coatings 737, 739 are formed from different materials and may define different thicknesses and/or overall volumes. Inner ferromagnetic coating 737 may define a greater overall greater volume than outer ferromagnetic coating 739 and/or may be formed from a relatively high magnetic loss material (as compared to outer ferromagnetic coating 739) while outer ferromagnetic coating 739 is formed from a material having a relatively higher permeability (as compared to inner ferromagnetic coating 737). As a result of this configuration, current is more concentrated and generates high ohmic loss within outer ferromagnetic coating 739 while the rest of the current within the relatively larger volume of the inner ferromagnetic coating 737 generates more magnetic loss, e.g., hysteresis loss.

Thermal cutting wire 730 is configured for self-limiting temperature regulation to achieve and maintain a pre-determined temperature. More specifically, in the presence of a high-frequency alternating current, ferromagnetic materials generate large amounts of heat through the hysteresis of the magnetic field in the alternating current. Ferromagnetic materials also have a temperature where they cease to be ferromagnetic, referred to as the Curie temperature. Thus, once the material reaches the Curie temperature, the heating effect essentially ceases. That is, once the material ceases to be ferromagnetic, it becomes a much less effective heater thereby greatly decreasing its thermal output to the point where that temperature is maintained. Thus, the result is a heater that maintains a specific temperature based on its configuration and can be used to ensure sufficient heating and prevent overheating without the need for sensors, feedback mechanisms, and/or control loops. Further, in use, when the heated thermal cutting wire 730 contacts tissue and is cooled below the Curie temperature, e.g., by virtue of contact with the relatively cooler tissue, the ferromagnetic thermal cutting wire 730 again becomes ferromagnetic and once again becomes an effective heater to automatically heat back to the Curie temperature, thus providing self-regulation.

Inner and outer ferromagnetic coatings 737, 739 may be configured to define different Curie temperatures. More specifically, outer ferromagnetic coating 739 may define a Curie temperature that is less than the Curie temperature of inner ferromagnetic coating 737. As a result of this configuration, when the Curie temperature of the outer ferromagnetic coating 739 is first achieved, the output power does not immediately drop to zero (or close to zero); instead, the output power drops to a mid-point of power due to the fact that the inner ferromagnetic coating 737 maintains its magnetic properties and continues to be heated (via a lower output power) until it reaches its Curie temperature. The final temperature of thermal cutting wire 730 in such embodiments is between the Curie temperature of outer ferromagnetic coating 739 and the Curie temperature of inner ferromagnetic coating 737, while the transition of output power (from the relatively high power when both coatings 737, 739 are being heated to the relatively lower output power when only inner coating 737 is being heated) is relatively smooth.

Thermal cutting wire 730 may further include an electrically insulative, e.g., ceramic, coating surrounding at least a portion of the outer ferromagnetic coating 739. Thermal cutting wire 730 may include a single exposed wire portion or multiple wire portions formed form multiple strands of wire or a single wire folded back onto, under, or along itself. Other configurations including non-wire ferromagnetic cutting elements, are also contemplated.

Figure 8:
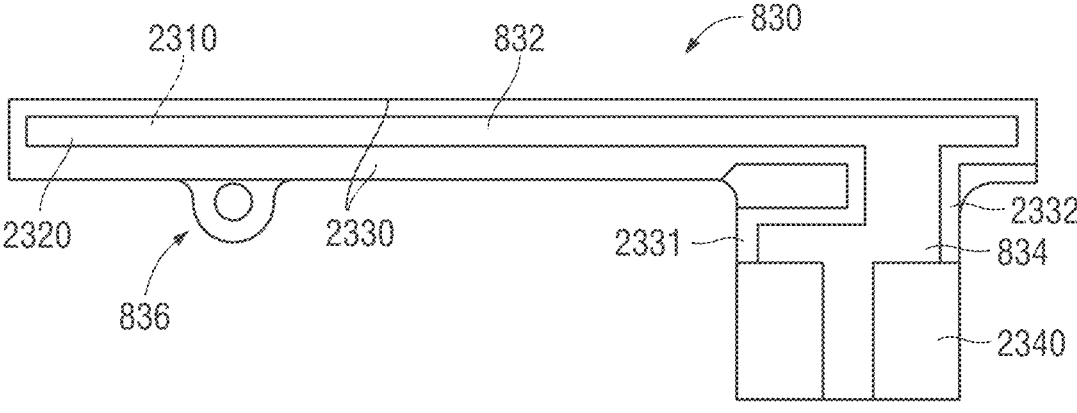
FIG. 8 is a side view of another thermal cutting element configured for use with the end effector assembly of FIG. 4.

With reference to FIG. 8, thermal cutting element 130 (FIGS. 4-6) may alternatively be configured as a thermal cutting element 830 having an aluminum substrate at least a portion of which is Plasma Electrolytic Oxidation (PEO)-treated with a heating layer affixed thereto such that when an AC voltage is applied, the thermal cutting element 830 is heated for thermally cutting tissue in contact therewith. More specifically, thermal cutting element 830 may include a substrate 2310, a PEO coating 2320 disposed about substrate 2310, a heating layer 2330 disposed on the PEO coating 2320 to form a heating element circuit including first and second end portions 2331, 2332, and first and second contacts 2340 electrically coupled to the respective first and second end portions 2331, 2332 of heating layer 2330. Thermal cutting element 830 defines an elongated body 832, a proximal connection flange 834 extending from a proximal end portion of elongated body 832, and one or more attachment flanges 836 extending from elongated body 832, e.g., from a central or distal end portion of elongated body 832. First and second end portions 2331, 2332 of heating layer 2330 are disposed at proximal connection flange 834. Heating layer 2330 defines a continuous circuit trace including first and second spaced-apart segments extending from first and second end portions 2331, 2332, respectively, distally along elongated body 832 to or adjacent a distal end portion of elongated body 832, wherein the first and second segments are interconnected with one another via a connector segment of heating layer 2330.

First and second contacts 2340 are affixed to first and second end portions 2331, 2332, respectively, of heating layer 2330 at proximal connection flange 834 to enable connection of electrical lead wires thereto for applying an AC voltage thereto to heat thermal cutting element 830. Proximal connection flange 834 may extend orthogonally relative to a longitudinal axis of elongated body 832, although other configurations are also contemplated.

In use, with tissue in contact with thermal cutting element 830 and an AC voltage applied across first and second contacts 2340 to thereby heat thermal cutting element 230, a thermal gradient is established whereby, as a result of the configuration of thermal cutting element 830, heat is conducted from portions of thermal cutting element 830 not in contact with tissue to those portions that are in contact with tissue. This facilitates heating and controlling the temperature of the portion of thermal cutting element 830, e.g., the body portion or the distal probe portion, that is in contact with tissue, thus facilitating control of the cutting (or other thermal treatment) of tissue.

Other suitable thermal cutting elements are also contemplated.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
an end effector assembly, including:
first and second jaw members each including an electrically conductive tissue-contacting surface, at least one of the first or second jaw members movable relative to the other from a spaced-apart position to an approximated position to grasp tissue between the tissue-contacting surfaces, the first and second jaw members adapted to connect to a source of energy for electrosurgically treating tissue grasped between the tissue-contacting surfaces; and
a thermal cutting element having a body portion extending along at least a portion of a length of the tissue-contacting surface of the second jaw member and a distal probe portion extending distally from the body portion, wherein the distal probe portion extends distally beyond a distal-most extent of the second jaw member such that a free end of the distal probe is distally-spaced from the distal-most extent of the second jaw member, the distal probe portion exposed about an entire outer periphery thereof along a length defined between the distal-most extent of the second jaw member and the free end of the distal probe portion, wherein the thermal cutting element comprises a conductive heating element that extends into the distal probe portion of the thermal cutting element and includes a first end portion connected to a first electrical contact and a second end portion connected to a second electrical contact such that a voltage applied across the first end portion and the second end portion heats the conductive heating element for thermally treating tissue positioned distally of the first and second jaw members.

2. The electrosurgical instrument according to claim 1, wherein the tissue-contacting surfaces of the first and second jaw members are configured to conduct RF energy therebetween and through tissue to seal tissue grasped between the tissue-contacting surfaces.

3. The electrosurgical instrument according to claim 1, wherein the conductive heating element is a ferromagnetic cutting element.

4. The electrosurgical instrument according to claim 3, wherein the ferromagnetic cutting element is a ferromagnetic cutting wire.

5. The electrosurgical instrument according to claim 3, wherein the ferromagnetic cutting element provides automatic Curie temperature control upon supply of energy thereto.

6. The electrosurgical instrument according to claim 1, wherein the conductive heating element is disposed on a substrate that is at least partially Plasma Electrolytic Oxidation (PEO)-treated.

7. The electrosurgical instrument according to claim 1, wherein thermal cutting element is configured to establish a thermal gradient to conduct heat from portions of the thermal cutting element not in contact with tissue to portions of the thermal cutting element in contact with tissue.

8. The electrosurgical instrument according to claim 1, wherein the body portion of the thermal cutting element and the distal probe portion of the thermal cutting element are collectively activatable.

9. The electrosurgical instrument according to claim 1, wherein the body portion of the thermal cutting element and the distal probe portion of the thermal cutting element are independently activatable.

10. The electrosurgical instrument according to claim 1, further comprising:
a housing having a shaft extending distally therefrom, wherein the end effector assembly is disposed at a distal end of the shaft.

11. The electrosurgical instrument according to claim 1, wherein the end effector assembly is adapted to connect to an arm of a robotic surgical system.

12. The electrosurgical instrument according to claim 1, further comprising:
first and second shafts coupled to one another about a pivot, wherein the end effector assembly is disposed at distal ends of the first and second shafts.

* * * * *